(12) United States Patent
Nahama

(10) Patent No.: US 12,144,886 B2
(45) Date of Patent: Nov. 19, 2024

(54) PERINEURAL ADMINISTRATION OF RESINIFERATOXIN FOR TREATMENT OF MALADAPTIVE PAIN

(71) Applicant: Sorrento Therapeutics, Inc., San Diego, CA (US)

(72) Inventor: Alexis Nahama, San Diego, CA (US)

(73) Assignee: Vivasor, Inc., San Diego, CA (US)

( * ) Notice: Subject to any disclaimer, the term of this patent is extended or adjusted under 35 U.S.C. 154(b) by 541 days.

(21) Appl. No.: 17/345,545

(22) Filed: Jun. 11, 2021

(65) Prior Publication Data
US 2021/0393515 A1  Dec. 23, 2021

Related U.S. Application Data

(63) Continuation of application No. PCT/US2019/068030, filed on Dec. 20, 2019.

(60) Provisional application No. 62/784,212, filed on Dec. 21, 2018.

(51) Int. Cl.
| | | |
|---|---|---|
| *A61K 9/00* | (2006.01) | |
| *A61K 31/357* | (2006.01) | |
| *A61K 47/02* | (2006.01) | |
| *A61K 47/10* | (2017.01) | |
| *A61K 47/26* | (2006.01) | |
| *A61P 29/02* | (2006.01) | |

(52) U.S. Cl.
CPC .......... *A61K 9/0019* (2013.01); *A61K 31/357* (2013.01); *A61K 47/02* (2013.01); *A61K 47/10* (2013.01); *A61K 47/26* (2013.01); *A61P 29/02* (2018.01)

(58) Field of Classification Search
CPC .... A61K 9/0019; A61K 31/357; A61K 47/02; A61K 47/10; A61K 47/26; A61K 47/36; A61P 29/02; A61P 25/02; A61P 25/04; A61P 25/00; C12N 15/82
See application file for complete search history.

(56) References Cited

U.S. PATENT DOCUMENTS

| | | |
|---|---|---|
| 7,432,275 B2 | 10/2008 | Bakthavatchalam et al. |
| 8,338,457 B2 | 12/2012 | Iadarola et al. |
| 9,827,223 B2 | 11/2017 | Iadarola et al. |
| 2004/0156931 A1 | 8/2004 | Burch et al. |
| 2005/0215575 A1 | 9/2005 | Bakthavatchalam et al. |
| 2007/0036876 A1 | 2/2007 | Burch et al. |
| 2008/0139641 A1 | 6/2008 | Meyer |
| 2010/0222385 A1 | 9/2010 | Iadarola et al. |
| 2015/0190509 A1 | 7/2015 | Giller |
| 2017/0296506 A1 | 10/2017 | Zucker et al. |
| 2021/0393515 A1 | 12/2021 | Nahama |
| 2022/0096428 A1 | 3/2022 | Nahama et al. |
| 2023/0270713 A1 | 8/2023 | Nahama et al. |

FOREIGN PATENT DOCUMENTS

| | | | |
|---|---|---|---|
| CA | 2594202 A1 | 7/2006 | |
| JP | 5775246 B2 | 9/2015 | |
| WO | 9909970 A1 | 3/1999 | |
| WO | 2006069451 A1 | 7/2006 | |
| WO | WO-2008109026 A1 * | 9/2008 | ............. A61K 31/12 |
| WO | 2017087803 A1 | 5/2017 | |
| WO | 2020132553 A1 | 6/2020 | |
| WO | 2020139797 A1 | 7/2020 | |
| WO | 2022245791 A1 | 11/2022 | |

OTHER PUBLICATIONS

Meyer et al. (JP5775246B2 Machine English Translation) (Year: 2015).*
Bates, et al. "Prolonged analgesic response of cornea to topical resiniferatoxin, a potent TRPV1 agonist," 149(3):522-528 (2010).
Benito et al. "Feline Musculoskeletal Pain Index: Responsiveness and Testing of Criterion Validity," Journal of Veterinary Internal Medicine, 27: 474-482 (2013).
Brown "Resiniferatoxin: The Evolution of the 'Molecular Scalpel' for Chronic Pain Relief," Pharmaceuticals (Basel), 9(3), pii E47 (2016).
Brown et al. "Intrathecal resiniferatoxin in a dog model: Efficacy in bone cancer pain," Pain, 156(6): 1018-1024 (2015).
Brown et al. "Physiologic and Antinociceptive Effects of Intrathecal Resiniferatoxin in a Canine Bone Cancer Model," Anesthesiology, 103: 1052-1059 (2005).
Currow et al. "Defining refractory pain in cancer for clinicians and researchers," J Palliat Med, 15(1): 5-6 (2012).
Deshpande et al. "Number of Persons With Symptomatic Knee Osteoarthritis in the US: Impact of Race and Ethnicity, Age, Sex, and Obesity," 68(12): 1743-1750 (2016).
Enomoto et al. "Defining the local nerve blocks for feline distal thoracic limb surgery: a cadaveric study," 18(10): 838-845 (2016).
Iadarola et al. "Long-term pain relief in canine osteoarthritis by a single intra-articular injection of resiniferatoxin, a potent TRPV-1 agonist," Pain, 159(10): 2105-2114 (2018).
Iadarola et al. "Resiniferatoxin for pain treatment: an interventional approach to personalized pain medicine," The Open Pain Journal, 6: 95-107 (2013).
Karai et al. "Deletion of vanilloid receptor 1-expressing primary afferent neurons for pain control" Journal of Clinical Investigation, 113(9): 1344-1352 (2004).
Kissin "Vanilloid-Induced Conduction Analgesia: Selective, Dose-Dependent, Long-Lasting, With A Low Level of Potential Neurotoxicity," Anesth. Analg 107(1): 271-281 (2008).
March et al. "Effects of resiniferatoxin on the neurogenic component of feline interstitial cystitis," Urology, (6 Suppl 1):114 (2001).
Martell-Moran NK., Solano M., Townsend HG. Pain and adverse behavior in declawed cats. Journal of Feline Medicine and Surgery, 20(4) 280-288 (2017).
Mourtzoukou et al. "Resiniferatoxin in the treatment of interstitial cystitis: a systematic review," International Urogynecological Journal, 19: 1571-1576 (2008).

(Continued)

*Primary Examiner* — Robert A Wax
*Assistant Examiner* — Quanglong N Truong
(74) *Attorney, Agent, or Firm* — McNeill PLLC

(57) ABSTRACT

Disclosed herein are methods of administering resiniferatoxin (RTX) perineurally for treatment of maladaptive pain, and compositions for use in such methods.

20 Claims, No Drawings

(56) References Cited

OTHER PUBLICATIONS

Neubert et al. "Perineural resiniferatoxin selectively inhibits inflammatory hyperalgesia," Molecular Pain, 4(3): 1-10 (2008).
Neubert et al. "Peripherally induced resiniferatoxin analgesia" Pain, 104: 219-228 (2003).
Paltser et al. "TRPV1 Gates Tissue Access and Sustains Pathogenicity in Autoimmune Encephalitis," Molecular Medicine, 19: 149-159 (2013).
Patronek GJ. Assessment of claims of short- and long-term complications associated with onychectomy in cats. JAVMA, 219: 932-937 (2001).
PCT, International Search Report and Written Opinion for PCT/US2019/068030 dated Mar. 13, 2020, p. 1-8.
Tender et al. "Selective ablation of nociceptive neurons for elimination of hyperalgesia and neurogenic inflammation," Journal of Neurosurgery, 102(3): 522-525 (2005).
Ueda et al. "Preventive Effect of TRPV1 Agonists Capsaicin and Resiniferatoxin on Ischemia/Reperfusion-induced Renal Injury in Rats," Journal of Cardiovascular Pharmacology, 51(5): 513-520 (2008).
Van Den Beuken-Van Everdingen, et al. "Prevalence of pain in patients with cancer: a systematic review of the past 40 years," Annals of Oncology, 18: 1437-1449 (2007).
Wang et al. "Cardiac Sympathetic Afferent Denervation Attenuates Cardiac Remodeling and Improves Cardiovascular Dysfunction in Rats with Heart Failure" Hypertension, 64(4); 745-755 (2014).
Weintraub "Prickly Painkiller" Scientific America, 309(1): 14-14 (2013).
Yoshie et al. "Cardiac vanilloid receptor-1 afferent depletion enhances stellate ganglion neuronal activity and efferent sympathetic response to cardiac stress," Am J Physiol Heart Circ Physiol, 314(5): H954-H966 (2018).
Adrian et al, "Chronic maladaptive pain in cats: A review of current and future drug treatment options", Veterinary Journal, vol. 230, pp. 52-61 (2017).
EP, Extended European Search Report corresponding to European Patent Application No. 19900434.2, mailed Aug. 18, 2022, 9 pages.
EP, Extended European Search Report corresponding to European Patent Application No. 20744876.2, mailed Oct. 10, 2022, 10 pages.
Kissin et al: "Therapeutic Targeting of TRPVI by Resiniferatoxin, from Preclinical Studies to Clinical Trials", Current Topics in Medicinal Chemistry, vol. 11, No. 17, pp. 2159-2170 (2011).
Kim et al. "The effects of intra-articular resiniferatoxin on monosodium iodoacetate-induced osteoarthritic pain in rats," Korean Journal of Physiology and Pharmacology, 20(1), 129-136 (2016).
Bae et al., "Expression of vanilloid receptor TRPV1 in the rat trigeminal sensory nuclei," The Journal of Comparative Neurology 478 (2004) pp. 62-71.
Teater D., "Evidence for the efficacy of pain medications: Saving Jobs, Saving Lives, and Reducing Human Costs," 2014 (8 pages).
Downie et al., "A quantitative analysis of the afferent and extrinsic efferent innervation of specific regions of the bladder and urethra in the cat," Brain Research Bulletin 12 (1984) pp. 735-740.
Enriquez-Perez et al., "Streptozocin-induced type-1 diabetes mellitus result in decreased density of CGRP sensory and TH sympathetic nerve fibers that are positively correlated with bone loss at the mouse femoral neck," Neuroscience Letters 655 (2017) pp. 28-34.
Farfariello et al., "Resiniferatoxin induces death of bladder cancer cells associated with mitochondrial dysfunction and reduces tumor growth in a xenograft mouse model," Chemico-Biological Interactions vol. 224, pp. 128-135, Oct. 29, 2014 (8 pgs.).
Gunn-Moore et al., "Oral glucosamine and the management of feline idiopathic cystitis," Journal of Feline Medicine and Surgery, 2004 (6), pp. 219-225.
Igawa et al., "Intravesical High-Dose Resiniferatoxin for the Treatment of Interstitial Cystitis," 37th Annual Conference of the International Continence Society—Rotterdam, Aug. 24, 2007 (2 pages).
International Search Report and Written Opinion of International Application No. PCT/US2021/038038, dated Sep. 23, 2021 (14 pages).
International Search Report and Written Opinion of International Patent Application No. PCT/US2021/14361 mailed May 18, 2020, 8 pages.
International Search Report and Written Opinion to International Patent Application No. PCT/US2022/029584, mailed Aug. 3, 2022, 8 pages.
Jimenez-Andrade et al., "Capsaicin-sensitive sensory nerve fibers contribute to the generation and maintenance of skeletal fracture pain," Neuroscience 162 (4) (2009), pp. 1244-1254.
Kissin et al., "Memory of Pain: The Effect of Perineural Resiniferatoxin", Anesthesia & Analgesia, vol. 103, Issue 3, pp. 721-728 (2006).
Kraemer et al., "Lumbar epidural perineural injection: a new technique", European Spine Journal, vol. 6, pp. 357-361 (1997).
Peters et al., "Intravenous paclitaxel administration in the rat induces a peripheral sensory neuropathy characterized by macrophage infiltration and injury to sensory neurons and their supporting cells," Experimental Neurology 203 (2007) pp. 42-54.
Seki et al., "Intravesical Instillation of Resiniferatoxin for Neurogenic Bladder Dysfunction in A Patient With Myelodysplasia," The Journal of Urology, vol. 166, pp. 2368-2369, Dec. 2001 (2 pages).
Sharrad et al., "Quantitative immunohistochemical co-localization of TRPV1 and CGRP in Varicose axons of the murine oesophagus, stomach and colorectum," Neuroscience Letters 599 (2015) pp. 164-171.

* cited by examiner

PERINEURAL ADMINISTRATION OF RESINIFERATOXIN FOR TREATMENT OF MALADAPTIVE PAIN

This application is a continuation of International Application No. PCT/US2019/068030, filed Dec. 20, 2019, which claims the benefit of priority of U.S. Provisional Patent Application No. 62/784,212, filed Dec. 21, 2018, which is incorporated by reference herein for all purposes.

The present disclosure provides methods of treating maladaptive pain comprising administering resiniferatoxin (RTX) perineurally, and resiniferatoxin for use in such methods.

I. INTRODUCTION AND SUMMARY

RTX acts as an ultrapotent analog of capsaicin, the pungent principal ingredient of the red pepper. RTX is a tricyclic diterpene isolated from certain species of Eurphorbia. A homovanillyl group is an important structural feature of capsaicin and is the most prominent feature distinguishing resiniferatoxin from typical phorbol-related compounds. Native RTX has the following structure:

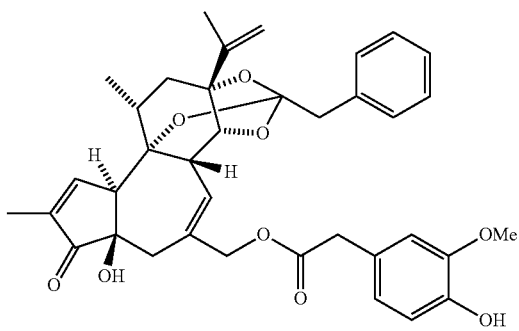 [SMILES: C=C(C)[C@]12C[C@@H](C)[C@@]34OC(Cc5ccccc5)(O[C@@H]1[C@@H]3C=C(COC(=O)Cc1ccc(O)c(OC)c1)C[C@]1(O)C(=O)C(C)=C[C@@H]41)O2]

RTX and analog compounds such as tinyatoxin and other compounds, (20-homovanillyl esters of diterpenes such as 12-deoxyphorbol 13-phenylacetate 20-homovanillate and mezerein 20-homovanillate) are described in U.S. Pat. Nos. 4,939,194; 5,021,450; and 5,232,684. Other resiniferatoxin-type phorboid vanilloids have also been identified (Szallasi et al. (1999) Brit. J. Pharmacol. 128:428-434).

RTX is known as a TrpV1 agonist. TrpV1, the transient receptor potential cation channel subfamily V member 1 (also known as Vanilloid receptor-1 (VR1)) is a multimeric cation channel prominently expressed in nociceptive primary afferent neurons (Caterina et al. (1997) Nature 389: 816-824; Tominaga et al. (1998) Neuron 21:531-543). Activation of TrpV1 typically occurs at the nerve endings via application of painful heat and is up regulated during certain types of inflammatory stimuli. Activation of TrpV1 in peripheral tissues by a chemical agonist results in the opening of calcium channels and the transduction of a pain sensation (Szalllasi et al. (1999) Mol. Pharmacol. 56:581-587). However, direct application of certain TrpV1 agonists to the cell body of a neuron (ganglion) expressing TrpV1 opens calcium channels and triggers a cascade of events leading to programmed cell death ("apoptosis") (Karai et al. (2004) J. of Clin. Invest. 113:1344-1352).

Maladaptive pain is pain that occurs despite healing and does not correlate to a present injury or other external pain source. It includes, but is not limited to, pain that arises in amputees such as phantom limb pain or stump pain, wherein misformation of neurons during the healing process can result in inappropriate neuronal connections and undesired activity of afferent nociceptive neurons. The pain experienced in phantom limb syndrome is an example of maladaptive pain. More generally, maladaptive pain may arise in any chronic condition in which an inappropriate amount of pain occurs and pain-modulation mechanisms in the central nervous system are implicated, e.g., following chronic or persistent afferent nociceptive neuron activity.

Treatment of maladaptive pain can be challenging. Systemic administration of painkillers is undesirable on a chronic basis due to concerns about side effects and/or dependency/addiction. Meanwhile, administration of pain-suppressing material directly at the site of the nociceptive nerve endings may require undesirably high and/or frequent doses. Additionally, intrathecal and epidural administrations carry a higher degree of risk due to proximity to the spinal cord. Nonetheless, existing publications implicate activity of the dorsal root ganglia and central nervous system in maladaptive pain such as phantom limb pain. See, e.g., Subedi et al., Pain Res. Treatment (2011) 2011:864605, 8 pages (discussing involvement of central neural changes involving cortical reorganization in mechanism of phantom limb pain); Borkum, J. Rat-Emo. Cognitive-Behav. Ther. (2010) 28:4-24 (discussing the role of maladaptive cognitions in chronic pain). Current thinking holds that the development of maladaptive pain initiates peripherally but results in sensitization in the central nervous system, at which point the sensitization becomes a persistent problem against which peripheral therapies are not expected to be successful. Thus, the current thinking leads to the expectation that treatments focused on elements of the nervous system peripheral to the dorsal root ganglia, without treating the dorsal root ganglia or central nervous system, may have low or less efficacy than treatments targeting the dorsal root ganglia or central nervous system. Accordingly, there is a need in the art to develop improved methods and compositions for use in treating maladaptive pain.

The present disclosure aims to meet this need and/or provide other benefits. Provided herein are methods of administering RTX perineurally for treatment of maladaptive pain to a subject in need thereof. This disclosure is based in part on the realization that perineural administration of RTX to treat maladaptive pain can provide effective pain relief at lower doses and/or lower dose frequency than treatments that target nociceptive nerve endings, e.g., in joint cavities, while also avoiding the risk associated with administration near the spinal cord. Perineural administration targets nerve fibers (axons) downstream from the nerve endings but upstream of the cell body (e.g., a sensory neuron cell body in a dorsal root ganglion).

Accordingly, the following exemplary embodiments are provided. Embodiment 1 is a method of treating maladaptive pain, comprising peripherally perineurally administering resiniferatoxin (RTX) to a subject in need of treatment of maladaptive pain.

Embodiment 2 is a composition comprising resiniferatoxin (RTX) for use in a method of treating maladaptive pain, the method comprising peripherally perineurally administering RTX to a subject in need of treatment of maladaptive pain.

Embodiment 3 is the method or composition for use according to embodiment 1 or 2, wherein the method comprises administering a dose of 0.1 µg to 100 µg of RTX. Embodiment 4 is the method or composition for use according to embodiment 3 wherein the dose of RTX ranges from 0.1-1 µg, 1-2 µg, 2-5 µg, 5-10 µg, 10-20 µg, 20-30 µg, 30-40 µg, 40-50 µg, 50-60 µg, 60-70 µg, 70-80 µg, 80-90 µg, or 90-100 µg.

Embodiment 5 is the method or composition for use according to any one of the preceding embodiments, wherein the RTX is administered perineurally to a single site. Embodiment 6 is the method or composition for use according to any one of the preceding embodiments, wherein the RTX is administered perineurally to a plurality of sites.

Embodiment 7 is the method or composition for use according to any one of the preceding embodiments, wherein the RTX is administered perineurally to the sciatic nerve. Embodiment 8 is the method or composition for use according to any one of the preceding embodiments, wherein the RTX is administered perineurally to the saphenous nerve. Embodiment 9 is the method or composition for use according to any one of the preceding embodiments, wherein the RTX is administered perineurally to the femoral nerve. Embodiment 10 is the method or composition for use according to any one of the preceding embodiments, wherein the RTX is administered perineurally to the radial nerve. Embodiment 11 is the method or composition for use according to any one of the preceding embodiments, wherein the RTX is administered perineurally to the ulnar nerve. Embodiment 12 is the method or composition for use according to any one of the preceding embodiments, wherein the RTX is administered perineurally to the median nerve. Embodiment 13 is the method or composition for use according to any one of the preceding embodiments, wherein the RTX is administered perineurally to the musculocutaneous nerve. Embodiment 14 is the method or composition for use according to any one of the preceding embodiments, wherein the RTX is administered perineurally to the palmar digital nerve.

Embodiment 15 is the method or composition for use according to any one of the preceding embodiments, wherein the RTX is administered perineurally to a plurality of sites that collectively correspond to sensory input from one or more digits. Embodiment 16 is the method or composition for use according to any one of the preceding embodiments, wherein the RTX is administered perineurally to a plurality of sites that collectively correspond to sensory input from a foot or hand. Embodiment 17 is the method or composition for use according to any one of the preceding embodiments, wherein the RTX is administered perineurally to a plurality of sites that collectively correspond to sensory input from a forelimb. Embodiment 18 is the method or composition for use according to any one of the preceding embodiments, wherein the RTX is administered perineurally to a plurality of sites that collectively correspond to sensory input from a limb. Embodiment 19 is the method or composition for use according to any one of the preceding embodiments, wherein the RTX is administered perineurally to a plurality of sites that collectively correspond to sensory input from a joint.

Embodiment 20 is the method or composition for use according to any one of the preceding embodiments, wherein the subject is an amputee. Embodiment 21 is the method or composition for use according to any one of the preceding embodiments, wherein perineural administration targets one or more nerve fibers downstream of an amputation site. Embodiment 22 is the method or composition for use according to any one of the preceding embodiments, wherein the subject suffers from phantom limb pain or stump pain. Embodiment 23 is the method or composition for use according to any one of embodiments 20-22, wherein perineural administration targets at least two, three, four, or five nerve fibers downstream of an amputation site.

Embodiment 24 is the method or composition for use according to any one of the preceding embodiments, wherein the subject has abnormal nerve growth at nerve endings. Embodiment 25 is the method or composition for use according to embodiment 24, wherein perineural administration targets one or more nerve fibers downstream of a nerve with abnormal growth at its peripheral ending. Embodiment 26 is the method or composition for use according to any one of the preceding embodiments, wherein perineural administration targets one or more nerve fibers downstream of a neuroma.

Embodiment 27 is the method or composition for use according to any one of the preceding embodiments, wherein the method comprises administering a pharmaceutical formulation comprising the RTX and a pharmaceutically acceptable carrier. Embodiment 28 is the method or composition for use of embodiment 27, wherein the pharmaceutically acceptable carrier comprises water. Embodiment 29 is the method or composition for use of embodiment 27 or 28, wherein the pharmaceutically acceptable carrier comprises polysorbate 80. Embodiment 30 is the method or composition for use of any one of embodiments 27-29, wherein the pharmaceutically acceptable carrier comprises polyethylene glycol. Embodiment 31 is the method or composition for use of any one of embodiments 27-30, wherein the pharmaceutically acceptable carrier comprises a sugar or sugar alcohol. Embodiment 32 is the method or composition for use of embodiment 31, wherein the pharmaceutically acceptable carrier comprises mannitol. Embodiment 33 is the method or composition for use of embodiment 31 or 32, wherein the pharmaceutically acceptable carrier comprises dextrose. Embodiment 34 is the method or composition for use of any one of embodiments 27-33, wherein the pharmaceutically acceptable carrier comprises a pharmaceutically acceptable buffer. Embodiment 35 is the method or composition for use of embodiment 34, wherein the pharmaceutically acceptable carrier comprises a phosphate buffer. Embodiment 36 is the method or composition for use of any one of embodiments 27-35, wherein the pharmaceutical formulation has a pH in the range of 6 to 7.6. Embodiment 37 is the method or composition for use of embodiment 36, wherein the pharmaceutical formulation has a pH in the range of 6 to 6.4, 6.3 to 6.7, 6.4 to 6.8, 6.8 to 7.2, 7 to 7.4, or 7.2 to 7.6. Embodiment 38 is the method or composition for use of embodiment 36, wherein the pharmaceutical formulation has a pH of 6.5 or 7.2. Embodiment 39 is the method or composition for use of any one of embodiments 27-38, wherein the pharmaceutically acceptable carrier comprises a pharmaceutically acceptable salt. Embodiment 40 is the method or composition for use of embodiment 39, wherein the pharmaceutically acceptable salt is NaCl. Embodiment 41 is the method or composition for use of any one of embodiments 27-40, wherein the concentration of RTX in the pharmaceutical formulation is in the range of 0.02-0.1 µg/ml or 0.1 to 300 µg/ml. Embodiment 42 is the method or composition for use of embodiment 41, wherein the concentration of RTX in the pharmaceutical formulation is in the range of 0.02-0.1 µg/ml, 0.1-1 µg/ml, 1-5 µg/ml, 5-10 µg/ml, 10-20 µg/ml, 20-50 µg/ml, 50-100 µg/ml, 100-150 µg/ml, 150-200 µg/ml, 200-250 µg/ml, or 250-300 µg/ml. Embodiment 43 is the method or composition for use of embodiment 41 or 42, wherein the concentration of RTX in the pharmaceutical formulation is in the range of 150 to 250 µg/ml, or is about 200 µg/ml. Embodiment 43.1 is the method or composition for use of embodiment 41 or 42, wherein the concentration of RTX in the pharmaceutical formulation is in the range of 0.1-200 µg/ml, optionally wherein the concentration of RTX in the pharmaceutical formulation is in the range of 0.1-50 µg/ml. Embodiment 43.2 is method or composition for use of any one of the preceding embodiments, wherein the RTX is administered in an injection volume of 0.05-10 ml, optionally wherein the injection volume is in the range of 0.05-0.2 ml, 0.2-0.5 ml, 0.5-1 ml, 1-2 ml, 2-5 ml, or 5-10 ml.

Embodiment 44 is the method or composition for use of any one of the preceding embodiments, wherein the subject is a mammal. Embodiment 45 is the method or composition for use of embodiment 44, wherein the subject is a cat. Embodiment 46 is the method or composition for use of embodiment 44, wherein the subject is a dog. Embodiment 47 is the method or composition for use of embodiment 44, wherein the subject is a horse or pig. Embodiment 48 is the method or composition for use of embodiment 44, wherein the mammal is a ruminant. Embodiment 49 is the method or composition for use of embodiment 48, wherein the ruminant is a cow, sheep, or goat. Embodiment 50 is the method or composition for use of any one of embodiments 44-49, wherein the mammal is a domesticated mammal.

Embodiment 51 is the method or composition for use of embodiment 44, wherein the subject is a human.

Embodiment 52 is the method or composition for use of any one of the preceding embodiments, wherein the treatment reduces local and central effects of the maladaptive pain. Embodiment 53 is the method or composition for use of any one of the preceding embodiments, wherein the subject had one or more behavioral symptoms of maladaptive pain prior to treatment and the treatment reduces or eliminates the one or more behavioral symptoms.

II. DETAILED DESCRIPTION

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

A. Definitions

"Peripheral perineural administration" or simply "perineural administration" as used herein is administration to a nerve fiber between the peripheral nerve ending and the cell body. For example, perineural administration encompasses injection of an agent in sufficient proximity to a nerve fiber between the peripheral nerve endings and the nerve cell bodies that the agent contacts the nerve fiber.

"Maladaptive pain" refers to pain disproportionate to actual tissue damage that persists after the tissue has healed and/or in the absence of tissue damage so that the pain itself is a problem apart from any underlying current source of pain such as an injury. Maladaptive pain is distinct from neuropathic pain, which results from damage or disease affecting sensory neurons.

"Downstream," used with respect to a site of perineural administration, refers to a site along the axon that is distal from the nerve ending so that the nerve ending themselves are not contacted by the agent being administered.

A "ruminant" is a mammal that has a rumen. Examples of ruminants include, but are not limited to cattle, sheep, antelopes, deer, and giraffes.

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

B. Exemplary Methods and Compositions for Use

Provided herein are methods for treating maladaptive pain, comprising peripherally perineurally administering resiniferatoxin (RTX) to a subject in need of treatment of maladaptive pain. Also provided are compositions comprising RTX for use in a method of treating maladaptive pain, the method comprising peripherally perineurally administering RTX to a subject in need of treatment of maladaptive pain. The present disclosure is based in part on the realization that, despite statements in the literature (e.g., in Subedi et al. and Borkum, supra) that the dorsal root ganglia and central nervous system play substantial roles in maladaptive pain including the origin thereof, peripheral perineural administration of RTX can provide significant relief of maladaptive pain. Without wishing to be bound by any particular theory, peripherally perineurally administering RTX may interrupt signals carried by afferent nociceptive neurons to a sufficient degree and for a sufficient duration to provide not only local but also central neurological effects that result in long-term reduction or control of maladaptive pain without the need for direct treatment of the dorsal root ganglia or central nervous system, contrary to the notion that maladaptive pain involves sensitization in the central nervous system as a persistent problem unlikely to be addressed through peripheral treatments. Thus, administration of RTX to treat maladaptive pain via a perineural route as disclosed herein may provide benefits that could not have been predicted from the literature, such as allowing effective pain relief without treatment of the dorsal root ganglia or central nervous system or systemic treatment and the attendant risks thereof, and/or with reduced dosage and/or frequency relative to treatments that target nociceptive nerve endings (e.g., in joint cavities, skin, or muscles).

1. Subjects

The compositions and methods described herein are for use with any subject in whom RTX is effective, e.g., able to bind and activate TrpV1 or a homolog thereof, and who is in need of treatment for maladaptive pain. In some embodiments, the subject is a mammal. In some embodiments, the mammal is a human. In some embodiments, the mammal is a cat. In some embodiments, the mammal is a dog. In some embodiments, the mammal is a ruminant. In some embodiments, the mammal is a horse, cow, pig, sheep, or goat.

In some embodiments, the subject is an amputee. In some embodiments, the subject suffers from phantom limb pain. For example, the phantom limb pain may occur at the site of an amputated finger, hand, forearm, arm, toe, foot, leg, or portion thereof (e.g., for the leg, above or below the knee). In some embodiments, the subject suffers from stump pain. For example, the phantom limb pain may occur at the end of a residual limb following amputation, e.g., of an amputated finger, hand, forearm, arm, toe, foot, leg, or portion thereof (e.g., for the leg, above or below the knee). Another example of a subject that may have phantom limb pain or stump pain is a de-clawed animal, e.g., cat. In some embodiments, the subject has abnormal nerve growth at nerve endings. For example, the abnormal growth at a nerve ending may be a neuroma.

In some embodiments, the subject had one or more behavioral symptoms of maladaptive pain prior to treatment and the treatment reduces or eliminates the one or more behavioral symptoms. For example, in domesticated animals, behavioral symptoms of maladaptive pain include behavioral issues such as aggressivity when manipulated, or diminished attention seeking (not seeking petting), and in cats, elimination behavior issues (e.g., urinating or defecating outside the litter box, not digging and burying elimination in the litter box).

2. Sites of Administration

RTX may be administered perineurally to one or more than one site, depending on the nerves responsible for the maladaptive pain. In some embodiments, the RTX is administered perineurally to a single site.

In some embodiments, the RTX is administered perineurally to the femoral nerve. In some embodiments, the RTX is administered perineurally to the sciatic nerve. In some embodiments, the RTX is administered perineurally to the saphenous nerve. In some embodiments, the RTX is administered perineurally to the radial nerve. In some embodiments, the RTX is administered perineurally to the ulnar nerve. In some embodiments, the RTX is administered perineurally to the median nerve. In some embodiments, the RTX is administered perineurally to the musculocutaneous nerve. In some embodiments, the RTX is administered perineurally to the palmar digital nerve. The sciatic nerve runs from the lower back to the legs (hind legs in the case of quadrupeds). The saphenous nerve is the largest cutaneous branch of the femoral nerve and is located in the lower leg (lower hindlimb in the case of quadrupeds). The femoral nerve is located in the upper thigh of the leg (upper hindlimb in the case of quadrupeds). The radial nerve is located in the upper arm (upper forelimb in the case of quadrupeds). The ulnar nerve is located in the forearm and the hand (forelimb in the case of quadrupeds). The median nerve is located in the upper arm (forelimb in the case of quadrupeds). The musculocutaneous nerve is located in the arm (forelimb in the case of quadrupeds) and branches off from the median nerve in the middle of the humerus. The palmar digital nerves are located in the hand (in the terminal segment of the forelimb in the case of quadrupeds).

In some embodiments, the RTX is administered perineurally to a plurality of sites. For example, treating the sciatic and saphenous nerves would block leg pain, treating the ulnar and palmar digital nerves would block hand pain, and treating the radial and median nerves would block upper arm pain. In some embodiments, the RTX is administered perineurally to a plurality of sites that collectively correspond to sensory input from one or more digits. In some embodiments, the RTX is administered perineurally to a plurality of sites that collectively correspond to sensory input from a foot or hand. In some embodiments, the RTX is administered perineurally to a plurality of sites that collectively correspond to sensory input from a forelimb (e.g., forearm or lower leg). In some embodiments, the RTX is administered perineurally to a plurality of sites that collectively correspond to sensory input from a limb (e.g., arm or leg). In some embodiments, the RTX is administered perineurally to a plurality of sites that collectively correspond to sensory input from a joint. In some embodiments, a plurality of sites includes a plurality of branches of a nerve (e.g., the dorsal and palmar branches of the ulnar nerve).

In some embodiments, the (RTX) is administered by injection. Injections may be performed, e.g., using a 1 cc syringe, or more generally, a size of syringe appropriate for the dosage volume.

3. Dosage

In some embodiments, the RTX is administered at a dose of 0.1-100 µg. In some embodiments, the dose of RTX ranges from 0.1-0.5 µg, 0.5-1 µg, 1-2 µg, 2-5 µg, 5-10 µg, 10-20 µg, 20-30 µg, 30-40 µg, 40-50 µg, 50-60 µg, 60-70 µg, 70-80 µg, 80-90 µg, or 90-100 µg. For example, e.g., in de-clawed cats, a total dose of 2.5 µg may be perineurally administered to one or both forelimbs. In humans, in some embodiments, a dose of up to 25 µg (e.g., 5-10 µg, 10-15 µg, 15-20 µg, or 20-25 µg; or about 5, 10, 15, 20, or 25 µg) is administered. In some embodiments, a 2-, 3-, or 4-point nerve block technique is used, with a total dosage in any of the ranges listed above, such as a total dosage of 0.5-1 µg, 1-2 µg, 2-5 µg, 5-10 µg, 10-15 µg, 15-20 µg, or 20-25 µg.

The dosage and volume can be adjusted depending on the proximity of the site of administration to the nerve fiber. For example, where ultrasound or a nerve stimulator is used to ensure that the site of administration is very close to the nerve, a lower dose and volume can be used. Alternatively, a nerve block such as a scapular or sciatic block can be accomplished using a larger volume such as 3-5 ml to ensure contact with the desired nerves. Notably, RTX is specific for the TRPV1 receptor and therefore does not affect non-target nerves such as motor neurons that do not have enough TRPV1 receptors to be sensitive to RTX.

4. Formulations

Multiple examples of formulations of RTX are available in the literature. See, e.g., Ueda et al. (2008) *J. of Cardiovasc. Pharmacol.* 51:513-520, and US 2015/0190509 A1. Any suitable formulation of RTX for parenteral administration (e.g., injection) may be used.

In some embodiments, the RTX, which may be at the dosages discussed above, is administered with a pharmaceutically acceptable carrier. In some embodiments, the pharmaceutically acceptable carrier comprises water. In some embodiments, the pharmaceutically acceptable carrier comprises polysorbate 80. In some embodiments, the pharmaceutically acceptable carrier comprises polyethylene glycol. In some embodiments, the pharmaceutically acceptable carrier comprises sugar or sugar alcohol. In some embodiments, the pharmaceutically acceptable carrier comprises mannitol. In some embodiments, the pharmaceutically acceptable carrier comprises dextrose. In some embodiments, the pharmaceutically acceptable carrier comprises a pharmaceutically acceptable buffer. In some embodiments, the pharmaceutically acceptable carrier comprises a phosphate buffer. In some embodiments, the pharmaceutically acceptable carrier comprises a pharmaceutically acceptable salt. In some embodiments, the pharmaceutically acceptable carrier comprises NaCl. In some embodiments, the pharmaceutically acceptable carrier comprises an organic solvent such as ethanol or DMSO, e.g., as a minority or residual component used as an aid in dissolving RTX before dilution in a primarily aqueous composition.

The concentration of RTX in the formulation may be any suitable value for delivery of the intended dose. In some embodiments, the concentration of RTX in the pharmaceutical formulation is in the range of 0.1 to 300 µg/ml. In some embodiments, the concentration of RTX in the pharmaceutical formulation is in the range of 0.1-1 µg/ml, 1-5 µg/ml, 5-10 µg/ml, 10-20 µg/ml, 10-30 µg/ml, 20-30 µg/ml, 20-50 µg/ml, 50-100 µg/ml, 100-150 µg/ml, 150-200 µg/ml, 200-250 µg/ml, or 250-300 µg/ml. In some embodiments, the concentration of RTX in the pharmaceutical formulation is in the range of 150 to 250 µg/ml, or 200 µg/ml. In some embodiments, the concentration of RTX in the pharmaceutical formulation is in the range of 0.1 to 200 µg/ml, such as 0.1 to 50 µg/ml or 50 to 200 µg/ml, or about 0.1, 0.2, 0.5, 1, 1.5, 2, 5, 10, 20, 25, 50, 100, or 200 µg/ml.

The formulation may have any pH suitable for perineural administration. In some embodiments, the pharmaceutical formulation comprising the RTX and a pharmaceutically acceptable carrier has a pH in the range of 6 to 7.6. In some embodiments, the pharmaceutical formulation comprising the RTX and a pharmaceutically acceptable carrier has a pH in the range of 6 to 6.4, 6.3 to 6.7, 6.4 to 6.8, 6.8 to 7.2, 7 to 7.4, or 7.2 to 7.6. In some embodiments, the pharmaceutical formulation comprising the RTX and a pharmaceutically acceptable carrier has a pH of 6.5 or 7.2.

In some embodiments, the formulation comprises polysorbate 80 and dextrose. In some embodiments, the concentration of polysorbate 80 is 2-4% w/v, and/or the concentration of dextrose is 4-6% w/v. In some embodiments, the concentration of polysorbate 80 is 3% w/v, and/or the concentration of dextrose is 5% w/v. In some embodiments, in any of the foregoing formulations, the concentration of RTX may be 10-30 µg/ml, such as 10 µg/ml or 25 µg/ml. In some embodiments, the formulation further comprises phosphate buffer, e.g., at a concentration and pH shown for phosphate buffer in Table 1. In some embodiments, the formulation further comprises NaCl, e.g., at a concentration shown for NaCl in Table 1. When both are present, the phosphate buffer and NaCl may be (but are not necessarily) present at a combination of concentrations and phosphate buffer pH shown for an individual formulation.

Exemplary formulations of RTX are shown in the following table.

TABLE 1

Exemplary RTX Solution Formulations

| Formulation Number | Formulation Components | Component Concentration |
|---|---|---|
| 1 | RTX | 200 µg/mL |
|  | Polysorbate 80 | 7.0% w/v |
|  | Dextrose | 0.8% w/v |
|  | 30 mM Phosphate Buffer w/0.44% NaCl | 30 mM, pH 7.2 |
| 2 | RTX | 200 µg/mL |
|  | Polyethylene Glycol 300 | 3.0% v/v |
|  | Polysorbate 80 | 0.1% w/v |
|  | Dextrose | 0.8% w/v |
|  | 10 mM Phosphate Buffer w/0.73% NaCl | 10 mM, pH 6.5 |
| 3 | RTX | 200 µg/mL |
|  | Polyethylene Glycol 300 | 30.0% v/v |
|  | Polysorbate 80 | 1.0% w/v |
|  | 10 mM Phosphate Buffer w/0.86% NaCl | 10 mM, pH 6.5 |
| 4 | RTX | 200 µg/mL |
|  | Polyethylene Glycol 300 | 30.0% v/v |
|  | Polysorbate 80 | 0.04% w/v |
|  | 10 mM Phosphate Buffer w/0.88% NaCl | 10 mM, pH 6.5 |
| 5 | RTX | 200 µg/mL |
|  | Polysorbate 80 | 3.0% w/v |
|  | Dextrose | 0.8% w/v |
|  | 30 mM Phosphate Buffer w/0.54% NaCl | 30 mM, pH 7.2 |
| 6 | RTX | 200 µg/mL |
|  | Polysorbate 80 | 3.0% w/v |
|  | Mannitol | 0.8% w/v |
|  | 30 mM Phosphate Buffer w/0.54% NaCl | 30 mM, pH 7.2 |
| 7 | RTX | 200 ug/mL |
|  | Polysorbate 80 | 7.0% w/v |
|  | Mannitol | 0.8% w/v |
|  | 30 mM Phosphate Buffer w/0.45% NaCl | 30 mM, pH 7.2 |
| 8 | RTX | 200 µg/mL |
|  | Polyethylene Glycol 300 | 3.0% v/v |
|  | Polysorbate 80 | 0.1% w/v |
|  | Mannitol | 0.8% w/v |
|  | 10 mM Phosphate Buffer w/0.74% NaCl | 10 mM, pH 6.5 |
| 9 | RTX | 200 µg/mL |
|  | Polyethylene Glycol 300 | 3.0% v/v |
|  | Polysorbate 80 | 0.1% w/v |
|  | Dextrose | 3.0% w/v |
|  | 10 mM Phosphate Buffer w/0.34% NaCl | 10 mM, pH 6.5 |
| 10 | RTX | 200 µg/mL |
|  | Polyethylene Glycol 300 | 3.0% v/v |
|  | Polysorbate 80 | 0.1% w/v |
|  | Mannitol | 3.0% w/v |
|  | 10 mM Phosphate Buffer w/0.36% NaCl | 10 mM, pH 6.5 |
| 11 | RTX | 200 µg/mL |
|  | Polysorbate 80 | 0.03% w/v |
|  | Dextrose | 0.05% w/v |
|  | 30 mM Phosphate Buffer w/0.54% NaCl | 30 mM, pH 7.2 |

In some embodiments, the concentration of RTX in a formulation shown in Table 1 is adjusted to any of the RTX concentrations or concentration ranges disclosed herein. For example, in some embodiments, the concentration of RTX in a formulation shown in Table 1 is adjusted to 10-50 µg/ml. As another example, in some embodiments, the concentration of RTX in a formulation shown in Table 1 is adjusted to 10-30 µg/ml. As another example, in some embodiments, the concentration of RTX in a formulation shown in Table 1 is adjusted to 20-30 µg/ml. As another example, in some embodiments, the concentration of RTX in a formulation shown in Table 1 is adjusted to 25 µg/ml. In some embodiments, the concentration of RTX in a formulation shown in Table 1 is adjusted to a concentration in the range of 0.1 to 100 µg/ml, or 0.1 to 50 µg/ml, such as 0.1 to 25 µg/ml, 25 to 50 µg/ml, or 50 to 100 µg/ml, or about 0.1, 0.2, 0.5, 1, 1.5, 2, 5, 10, 20, 25, 50, or 100 µg/ml.

The formulations in Table 1 may be prepared according to the following exemplary methods, which are provided for formulations 3 and 5 but may be adapted to the other formulations by one skilled in the art. Formulation 3 may be made by preparing a 30 mM, pH 7.2 phosphate buffer. Then 1.43% w/v polysorbate 80 and 0.86% w/v NaCl are mixed to form the aqueous component. 20 mg of RTX is added to 100 mL of the aqueous component in a volumetric flask. Then 30 mL of PEG 300 is added and the solution is sonicated to dissolve the solids. The aqueous component is added to about 80% volume, and then it is sonicated to mix. It should be noted that RTX will sometimes precipitate at the interface of aqueous solution and PEG initially, but will go back into solution upon sonication. The full mixture in the flask is diluted to volume with the aqueous component and this is mixed by an inversion process. The full formulation is filtered through a 0.2 μm polytetrafluoroethylene (PTFE) filter.

Formulation 5 may be made by preparing 30 mM, pH 7.2 phosphate buffer. Then 3.0% w/v polysorbate 80, 0.8% w/v dextrose, and 0.54% w/v NaCl are mixed together to form the aqueous component. 20 mg of RTX is added to 100 mL of the aqueous component in a volumetric flask. The aqueous component is added to about 80% volume, and then it is sonicated to dissolve all the solids. (Alternatively, the RTX may be initially dissolved in a small volume of ethanol or DMSO, and this solution may then be added to the aqueous component.) The full mixture in the flask is diluted to volume with the aqueous component and this is mixed by an inversion process. The full formulation is filtered through a 0.2 μm PTFE filter.

A formulation according to Formulation 11 is prepared using 200 μg RTX, 20 mg Polysorbate 80 (using commercially-available polysorbate 80); 5.4 mg of sodium chloride, 50 mg of dextrose, and a 30 mM aqueous phosphate buffer, water (WFI) to 1 mL.

In some embodiments, the pharmaceutical formulation is in a unit dosage form. In such form, the preparation is subdivided into unit doses containing appropriate quantities of the active component. The unit dosage form can be a packaged preparation, the package containing discrete quantities of formulation, such as in vials, ampoules, or preloaded syringes. Also, the unit dosage form can be, e.g., a solution or a lyophilized composition for reconstitution.

Further details on techniques for formulation and administration may be found in Gennaro, A., Ed., Remington's Pharmaceutical Sciences, 18th Ed. (1990) (Mack Publishing Co., Easton, Pa.).

III. EXAMPLES

A. Study Design for Perineural Administration Trial in Cats

As described herein, a loco-regional application of RTX will be used in a cohort of cats with refractory localized maladaptive pain to evaluate tolerance, safety, and analgesic effects as shown in Table 2.

TABLE 2

Study design

| Indication | Dose | Instructions | Effectiveness Assessment (at days 3, 7, and 14) | Safety Assessment (at screening and Day 14) |
|---|---|---|---|---|
| Declaw refractory pain (older than 90 days) Bilateral limb administration | 5 μg/cat or 2.5 μg/forelimb | 1 cc syringe with RTX (0.1 mL of RTX), with 0.9 mL added saline to 1 mL total injection volume | 1. Owner videography<br>2. Client specific outcome measure (CSOM)<br>3. Feline Musculoskeletal Pain Index (FMPI) | 1. Complete blood count<br>2. Chemistry Panel<br>3. Adverse Events |

Each dose of 5 μg/cat or 2.5 μg/forelimb will be formulated in 1 cc insulin syringes by diluting 0.1 mL: (2.5 μg) of RTX in 0.9 mL sterile saline for injection immediately before use. For treatment, a total of 1.0 mL (2.5 μg) will be injected as nerve blocks, distributed equally (0.25 ml per injection site) over 4 injection sites for each forelimb.

Inclusion criteria for the study includes the following: the cat has documented localized forelimb pain following declaw surgery; the cat is experiencing pain that is refractory to standard pain management or the owner has chosen to pursue pain management that is distinct from conventional treatment; the owner expresses that his or her cat has experienced a significant decrease in quality of life due to refractory pain, the owner reports behavioral issues related to the chronic maladaptive pain state such as elimination behavior issues (urinating or defecating outside the litter box, not digging and burying elimination in the litter box), aggressivity when manipulated, or diminished attention seeking (not seeking petting), and/or is considering euthanasia of their cat due to clinical signs related to refractory pain (i.e., pain and mobility are negatively impacting quality of life); medications commonly used for the treatment of pain (even if they have been prescribed for another reason; e.g., corticosteroids) are acceptable provided they have been administered for at least 2 weeks prior to enrolling in the study, and no changes in regimen are expected in the next 3 weeks; and the declaw procedure was performed at least 90 days before the day of treatment. The cat must also be at least 12 months of age, weigh at least 2 kg, and not be participating in another study or have impairments due to primary neurological disease.

A cat will be excluded from the study if the cat exhibits any of the following exclusion criteria: the cat is pregnant or lactating; the cat requires medication or supplements during the course of the study that may interfere with the objective of the study; or the severity of pain is rated less than 5 on a 10-point scale by the investigator at either Day −7 or Day 0 prior to treatment.

Four point nerve blocks are performed by injection of 0.25 mL RTX each into the 1) superficial branches of the radial nerve, 2) dorsal branch of the ulnar nerve, 3) median nerve and superficial branch of the palmar branch of the ulnar nerve, and 4) deep branch of the palmar branch of the ulnar nerve. The nerve blocks for each forelimb are performed following a published technique for locoregional block of the manus in cats (Enomoto et al. (2016) *J. Feline Med. Surg.* 18:838-845). To block the superficial branches of the radial nerve (RSbr nn), the limb is positioned with the dorsal aspect facing upwards and the carpus in 180° of extension. A 25 G×⅝-inch needle is inserted subcutaneously (SC) from a point at the center of the limb at the level of the antebrachiocarpal joint. The needle is advanced approximately 10 mm SC at a 10-20° angle to the long axis of the limb with the bevel facing up. Once the tip of the needle is 3-5 mm from the confluence point of the accessory cephalic and cephalic veins, the injection is made (0.25 mL). To block the dorsal branch of the ulnar nerve (UDbr n), the limb is positioned with the lateral aspect facing upwards. A point is located lateral to and at the same level as the accessory carpal bone (ACb), positioned between the ACb and the styloid process of the ulna (SpU). A 25 G×⅝-inch needle is inserted SC distal to proximal, so the tip lies at the midpoint of the groove formed between ACb and the SpU, and then the injection is made (0.25 mL). To block the median nerve (M n) and superficial branch of the palmar branch of the ulnar nerve (UPbrS n), the limb is positioned with the palmar aspect facing upwards. A 25 G×⅝-inch needle is inserted SC at the distal border of the carpal pad and approximately 5 mm lateral to it, perpendicular to the long axis of the metacarpus, with the bevel facing up. The needle is inserted SC until the point is located two-thirds of the distance from the lateral aspect of the limb to the medial aspect. Two-thirds of the injectate volume is deposited at this point and the remaining volume is injected while the needle is withdrawn (0.25 mL). Gentle massage is applied to the injected volume under the skin for 5 seconds. To block the deep branch of the palmar branch of the ulnar nerve (UPbrDp n), the limb is positioned with the palmar aspect facing upwards. A 25 G×⅝-inch needle is inserted almost perpendicular to the ACb in a mediolateral direction such that the needle contacts the medial palmar aspect of the midpoint of the ACb with the bevel facing up. The needle is then redirected dorsally and advanced on the medial side of the ACb 2-3 mm until it penetrates the flexor retinaculum, and then the injection is made (0.25 mL).

The effectiveness of the injection with RTX is assessed at days 3, 7, and 14 using owner videography for qualitative assessment (jumping, manipulation of the limb), and cats will also be evaluated using the Feline Musculoskeletal Pain Index (FMPI) and the Client Specific Outcome Measure (CSOM).

For CSOM, owners are asked to score three attributes (Q1) Extending distal limb, "kneading"; stretching, (Q2) Running; and (Q3) Jumping down from bed and window using a scale of 1-5 where 1=no problem, 2=mild difficulty, 3=moderate, 4=severe difficulty, and 5=impossible.

For FMPI, cats are scored for 17 attributes designated Q1-Q17 using a scale of 0-4, where 0=not at all, 1=barely or with great effort, 2=moderately worse than normal, 3=near normal, and 4=normal. The total FMPI score is the sum of scores for each question. Higher totals indicate less impairment with a possible range of (0-68). For analysis, total score or percent possible can be used. Q1-Q17 are as follows: walking (Q1), running (Q2), jumping up (Q3), jumping up to kitchen counter height (Q4), jumping down (Q5), climbing upstairs (Q6), going down stairs (Q7), playing with/chasing toys (Q8), playing and interacting with other pets (Q9), getting up from a resting position (Q10), lying or sitting down (Q11), stretching (Q12), grooming (Q13), interacting with the owner (Q14), being touched or handled (Q15), eating (Q16), and using the litter box (Q17).

The safety of the injection of RTX is assessed by comparing the results of a complete blood count (CBC) and a chemistry panel done at screening with the results obtained at day 14. Cats were also monitored for adverse events.

B. Perineural Administration to Declawed Cat Suffering from Maladaptive Pain

Tolerance, safety, and analgesic effects of RTX administration were evaluated in a single declawed cat with maladaptive pain. The cat received a total of 1.0 mL (2.5 µg) of RTX injected as nerve blocks, distributed equally (0.25 ml per injection site) over 4 injection sites for each forelimb as described above in Example A. No complications were observed during RTX administration. The injection of RTX was generally well tolerated. Adverse events of panting and salivation one hour post-injection were noted, and both of these events were resolved within two hours. The cat also presented a self-limiting decreased appetite for 12 hours post injection. No signs of allergic-like reactions were observed and no signs of edema or pain were present in the injected areas.

On the screening day, the cat presented with a total CSOM score of 8 and mild to moderate difficulty with Q1-Q3. By day 14 after injection with RTX, the CSOM score was a 6 with the cat experiencing mild difficulty with Q1-Q3. Extending distal limb, kneading, stretching and running all showed improvement in this cat. CSOM was also evaluated at days 7 and 14, which both showed improvement relative to day 3 as shown in Table 3.

TABLE 3

Difference in CSOM scores after a single injection of RTX

|  | Screening | Day 0 | Day 3 | Day 7 | Day 14 |
| --- | --- | --- | --- | --- | --- |
| Q1 Extending distal limb; "kneading"; stretching | 3 | 3 | 2 | *1* | *2* |
| Q2 Running | 3 | 3 | 3 | *2* | *2* |
| Q3 Jumping down from bed and window | 2 | 2 | 2 | 2 | 2 |
| Total | 8 | 8 | 7 | 5 | 6 |

CSOM (1 = no problem; 2 = mild difficulty; 3 = moderate; 4 = severe difficulty; 5 = impossible)
Cells without italicization indicate baseline or no change, and cells with italicized numbers indicate improvement.
No worsening of score was observed.

A summary of the pre- and post-RTX injection physical exam results relevant to pain related to the declawed digits are presented in Table 4.

TABLE 4

Summary of Physical Exam Findings

| Screening | Day 0 | Day 7 | Day 14 |
|---|---|---|---|
| Stifles range of motion decreased; Declawed digits contracted; Gait short and choppy; Walks a few steps then sits | Contracted thoracic limb digits | Resistance on digit palpitation but less dramatic | Contracted digits but less resistance on palpitation |

The analgesic effects of the single injection of RTX into a cat was evaluated using Feline Musculoskeletal Pain Index (FMPI) (Table 5). The total FMPI score is the sum of scores for each question. Higher totals indicate less impairment with a possible range of (0-68). For analysis, total score or percent possible can be used. On screening day and day 0, the cat had an FMPI score of 47. By day 14 post injection of RTX, the cat had a FMPI score of 57 indicating improvement. Calculation of percent possible is performed by taking the total score for the cat and dividing by the total possible points (i.e., the number of questions answered multiplied by 4). Thus, percent possible=(sum of Q1-17 scores)/(number of questions answered*4).

TABLE 5

The difference in FMPI scores after a single injection of RTX

| | Screening | Day 0 | Day 3 | Day 7 | Day 14 | Improved |
|---|---|---|---|---|---|---|
| Q1 | 2 | 2 | 3 | 3 | 3 | No change |
| Q2 | 1 | 1 | 2 | 3 | 3 | *Worse Baseline |
| Q3 | 3 | 3 | 3 | 3 | 4 | |
| Q4 | 0 | 0 | 2 | 3 | 3 | |
| Q5 | 2 | 2 | 3 | 3 | 3 | |
| Q6 | 4 | 4 | *3 | 4 | 4 | |
| Q7 | 4 | 4 | *3 | 4 | 4 | |
| Q8 | 3 | 3 | 3 | 3 | 3 | |
| Q9 | 2 | 2 | *1 | 2 | 3 | |
| Q10 | 4 | 4 | 4 | 4 | 4 | |
| Q11 | 4 | 4 | 4 | 4 | 4 | |
| Q12 | 3 | 3 | *2 | 3 | 3 | |
| Q13 | 3 | 3 | 3 | 3 | 3 | |
| Q14 | 3 | 3 | 3 | 3 | 3 | |
| Q15 | 2 | 2 | 2 | 3 | 3 | |
| Q16 | 4 | 4 | 4 | 4 | 4 | |
| Q17 | 3 | 3 | 3 | 3 | 3 | |
| Total | 47 | 47 | 48 | 55 | 57 | |
| FMPI % poss | 0.69 | 0.69 | 0.71 | 0.81 | 0.84 | |

FMPI (4 = normal; 3 = near normal; 2 = Moderately worse than normal; 1 = Barely, or with great effort; 0 = not at all)
Cells with white background and no italicization indicate baseline or no change, cells with italicization indicate improvement, and cells filled black indicate worsening of score.

Additionally, the cat had shown elimination behavior issues, aggressivity when manipulated, and diminished attention seeking before treatment. Each of these behavioral issues related to the chronic maladaptive pain state reversed following the perineural administration of RTX, even though the cat was believed to have been in pain for years prior to this treatment. These results are evidence that reduction of peripheral signaling can be sufficient to reverse central perception of maladaptive pain even in subjects likely to have sustained long term plasticity changes in the central nervous system in connection with maladaptive pain.

Thus, administration of RTX was safe and effective in this cat as shown by the improvement in CSOM and FMPI scores. Effects persisted for at least 14 days.

C. Study of Perineural Resiniferatoxin for Severe Chronic Distal Limb Pain in Declawed Cats Chronic distal limb pain in cats is detrimental to their quality of life (QoL). The purpose of this study was to evaluate the use of RTX as a sole perineural pain management modality in declawed cats with evidence of chronic distal thoracic limb pain.

During surgical or traumatic amputations, a substantial amount of trauma occurs in nerves and the surrounding tissue. This neural injury allows the sprouting of nerve endings, causing the terminals to become hyper-excitable, which is perpetuated and worsened by local inflammation.

The scientific evidence from human and feline patients suffering from post-amputation pain syndrome, suggests that the development of this multifactorial condition is tightly related to local neuroma formations and the subsequent alteration of peripheral and central neural pathways (Hanyu-Deutmeyer A A and Dulebohn S C. StatPearls [Internet]. Treasure Island (FL): StatPearls Publishing; 2018 January-2018 Apr. 17). The resemblance in pathophysiology and clinical presentation between feline and human patients transforms the feline post-declaw pain syndrome in an excellent translational tool to deepen our understanding of painful maladaptive diseases in humans like residual-limb pain and complex regional pain syndrome (CRPS).

Cats suffering from severe bilateral chronic pain (more than 90 days) as a result of severe complications after onychectomy were enrolled in this study (an exploratory, open-label, multicenter clinical trial). Thirteen (13) cases were treated for initial pain and reduced quality of life (QoL). Then, bilateral perineural distal limb injections (ring block technique) were administered under general anesthesia (a combination of diphenhydramine, buprenorphine, dexmedetomidine, ketamine, and isoflurane). Following a published technique (Enomoto et al., 2016) for the nerve block of the manus of the cat, the total dose of RTX was equally distributed adjacent to the 1) superficial branch of the radial nerve, 2) dorsal branch of the ulnar nerve, 3) median nerve and superficial branch of the palmar branch of the ulnar nerve, and 4) deep branch of palmar branch of the ulnar nerve. A total of 2.5 ug (1.25 ug/1 mL per forelimb in Group 1, n=7) and 5 ug (2.5 ug/1 mL per forelimb in Group 2, n=6) of RTX was injected as a one-time treatment. Group 2 included the cat for which detailed results are provided in Example B above. Monitoring of QoL and pain for the following 28 days was accomplished using the Client-Specific Outcome Measures feline (CSOMf), the Feline Musculoskeletal Pain Index (FMPI), two post-injection physical examinations, and videography on days 3, 7, 14, and 28 post injections.

In both groups (71.4% Group 1; 100% Group 2), animals experienced self-limiting reactions related to the treatment during the recovery from anesthesia. The most common adverse events (AEs) were panting (57.1% in Group 1; 83.3% in Group 2), vocalization (57.1% in Group 1; 83.3% in Group 2) and hypersalivation (71.4% in Group 1; 50% in Group 2), and they resolved within 4 hours after treatment. When analyzed by day of presentation and resolution, in both groups, more than 85% of the AEs were presented and resolved the same day of administration (Group 1=86.6% [26/30]; Group 2=95.4% [21/22]).

The CSOMf and FMPI scores showed a clear improvement over the 28-day monitoring period.

In both groups, owners reported significant changes in natural (i.e., improved socialization, kneading and physical activities) and pathological adopted behaviors (i.e., aggressivity towards owners and other pet in the same house, inappropriate urination and defecation) which are considered indicative of improvements in QoL. In some cases, these behavioral improvements allowed relinquished patients to be adopted and relocated into new homes. The formal monitoring period was 28 days, but improvements were reported informally for several months (over 6 months) in some cases. It was reported for at least two cats that the improvement lasted for months, included improved demeanor and reduction in negative behavior, and reduced or eliminated the need for daily systemic medications.

Thus, this study provides evidence that perineural injections of RTX for chronic pain management can effectively treat cats with distal thoracic limb pain negatively affecting their quality of life, and furthermore that perineural RTX at the described doses was well tolerated in these cats.

D. A Single Dose Study of Resiniferatoxin as a Nerve Block Injection in Rats with a 14-Day Recovery Period This study was directed to determining the safety of administering RTX, when given as a nerve block injection as a single dose to rats.

The study design was as follows:

TABLE 6

Experimental Design - Main and Recovery Study

| Group Number | Test Material | Dose Level (µg) | Dose Volume (mL) | Dose Concentration (µg/mL) | Main Study Males | Main Study Females | Recovery Study Males | Recovery Study Females |
|---|---|---|---|---|---|---|---|---|
| 1 | Control Article 1[a] | 0 | 0.1 | 0 | 10 | 10 | 5 | 5 |
| 2 | Control Article 2[b] | 0 | 0.1 | 0 | 10 | 10 | 5 | 5 |
| 3 | Test Article 1[c] | 0.625 | 0.1 | 6.25 | 10 | 10 | 5 | 5 |
| 4 | Test Article 1[c] | 2.5 | 0.1 | 25 | 10 | 10 | 5 | 5 |
| 5 | Test Article 2[d] | 10 | 0.1 | 100 | 10 | 10 | 5 | 5 |

[a]0.9% Sodium Chloride for Injection, USP.
[b]30 mg/mL Tween 80, 1.38 mg/mL Sodium Phosphate Monobasic Monohydrate, 2.84 mg/mL Sodium Phosphate Dibasic Anhydrous, 50.0 mg/mL Dextrose Monohydrate, 5.4 mg/mL Sodium Chloride, 1 mL Sterile Water.
[c]25 µg/mL Resiniferatoxin.
[d]200 µg/mL Resiniferatoxin.

TABLE 7

Experimental Design - Toxicokinetic Study

| Group Number | Test Material | Dose Level (µg) | Dose Volume (mL) | Dose Concentration (µg/mL) | Toxicokinetic Study Males | Toxicokinetic Study Females |
|---|---|---|---|---|---|---|
| 1 | Control Article 1[a] | 0 | 0.1 | 0 | 3 | 3 |
| 2 | Control Article 2[b] | 0 | 0.1 | 0 | 3 | 3 |
| 3 | Test Article 1[c] | 0.625 | 0.1 | 6.25 | 9 | 9 |
| 4 | Test Article 1[c] | 2.5 | 0.1 | 25 | 9 | 9 |
| 5 | Test Article 2[d] | 10 | 0.1 | 100 | 9 | 9 |

[a]0.9% Sodium Chloride for Injection, USP.
[b]30 mg/mL Tween 80, 1.38 mg/mL Sodium Phosphate Monobasic Monohydrate, 2.84 mg/mL Sodium Phosphate Dibasic Anhydrous, 50.0 mg/mL Dextrose Monohydrate, 5.4 mg/mL Sodium Chloride, 1 mL Sterile Water.
[c]25 µg/mL Resiniferatoxin.
[d]200 µg/mL Resiniferatoxin.

Administration of resiniferatoxin as a nerve block injection was well tolerated in rats at levels of 0.625, 2.5, and 10 µg. The no-observed-adverse-effect level (NOAEL) was considered to be 10 µg.

119 male and 119 female Crl:CD(SD) Sprague Dawley rats were obtained from Charles River Laboratories, Raleigh, NC. The animals were 10 weeks old and weighed between 212 and 482 g at the initiation of dosing.

Male and female animals were separately assigned to groups in a randomized manner with stratification to achieve similar group mean body weights.

Before the initiation of dosing, assigned animals considered unsuitable for use in the study were replaced by alternate animals obtained from the same shipment and maintained under the same environmental conditions.

| | |
|---|---|
| Dose Route: | Nerve block injection |
| Frequency: | Once daily |
| Duration: | On Day 1 |
| Method: | The doses were given into the right thigh. The animals were temporarily restrained for dose administration. Animals were sedated via isoflurane inhalation for dose administration. The right thigh was clipped free of hair before the first dose and as often as necessary thereafter to allow for clear visualization of the test site. Care was taken during the clipping procedure to avoid abrasion of the |

-continued

| | |
|---|---|
| | skin. The injection site was marked with indelible ink and re-marked as often as needed. The day of dosing for each animal was designated as Day 1. |

The nerve block injection doses were given into the right thigh. The animals were temporarily restrained for dose administration. Animals were sedated via isoflurane inhalation for dose administration. The day of dosing for each animal was designated as Day 1. A necropsy was conducted for a recovery study animal that died on study, and specified tissues were retained. The animal was refrigerated prior to necropsy to minimize autolysis.

For humane reasons, a recovery study animal was euthanized. The animal underwent necropsy. The animal was refrigerated before necropsy to minimize autolysis.

Main study and recovery animals surviving until scheduled euthanasia on Day 2 had a terminal body weight recorded; samples were collected for evaluation of clinical pathology; and the animals were euthanized by isoflurane inhalation, followed by exsanguination. Toxicokinetic animals surviving until scheduled euthanasia were euthanized by carbon dioxide inhalation.

Main study and recovery animals were subjected to a complete necropsy examination. A board-certified veterinary pathologist was available for scheduled necropsies.

All statistical tests were conducted at the 5% significance level. All pairwise comparisons were conducted using two-sided tests.

The pairwise comparisons of interest are listed below:

| | | |
|---|---|---|
| Group 2 | vs. | Group 1 |
| Group 3 | vs. | Group 1 |
| Group 4 | vs. | Group 1 |
| Group 5 | vs. | Group 2 |

Analyses excluded any group with less than 3 observations.

Levene's test was used to assess the homogeneity of group variances.

The groups were compared using an overall one-way ANOVA F-test if Levene's test was not significant or the Kruskal-Wallis test if it was significant. If the overall F-test or Kruskal-Wallis test was found to be significant, then pairwise comparisons were conducted using Dunnett's or Dunn's test, respectively. Datasets with two groups were compared using a Dunnett's test (equivalent to t-test in Nevis 2012 tables) or Dunn's test (equivalent to Wilcoxon Rank-Sum test in Nevis 2012 tables).

RESULTS

Validated methods were used for the determination of RTX concentrations in the control and test formulations. RTX was not detected in any of the Group 1 and Group 2 (vehicle) samples. The mean concentrations in Groups 3 through 5 ranged from 93.6% to 117% of their theoretical concentrations.

There were no test article-related unscheduled deaths or gross observations.

There was an RTX (resiniferatoxin)-related statistically significant decrease in mean body weight gain at 10 µg from Days 1 to 2 in males and from Days 1 to 14 in females that corresponded to a decreased mean body weight compared to controls.

There was a statistically significant decrease in food consumption on Days 2 to 7 at 2.5 µg in females only and at 10 µg in males only.

Various statistically significant differences in certain leukocyte numbers, platelet count, fibrogin, aspartate aminotransferase and alanine aminotransferase, total protein, albumin, albumin/globulin ratio, phosphorus, specific gravity and triglycerides along with a few other parameters were noted; however, these differences were not considered adverse or were not considered vehicle or test article related due to 1 or more of the following: the absolute differences were minimal; the changes lacked a clear dose-response relationship; there was an absence of correlative microscopic findings; the absolute differences were minimal; and/or the changes lacked a clear dose-response relationship. Additionally, the differences generally resolved during the recovery period, except that neutrophils had a statistically significant increase that remained increased after the recovery period at 10 µg, in females only.

There were no adverse RTX (resiniferatoxin)-related changes in clinical chemistry parameters.

No test article-related gross findings were noted in the terminal euthanasia or recovery period animals. The gross findings observed were considered incidental, of the nature commonly observed in this strain and age of rats, and/or were of similar incidence in control and treated animals and, therefore, were considered unrelated to administration of RTX.

Statistically significant lower absolute and relative spleen weights were observed in both sexes administered 10 µg RTX. This correlated microscopically with minimal decreased lymphoid cellularity of the white pulp. Lower absolute and relative thymic weights in both sexes administered 10 µg RTX correlated microscopically with minimal to mild decreased lymphoid cellularity. No other test article-related organ weight changes were noted. Test article-related organ weight changes noted at the terminal euthanasia were not observed at the end of the recovery period (Day 15).

There were isolated organ weight values that were statistically different from their respective controls. There were, however, no patterns, trends or correlating data to suggest these values were toxicologically relevant. Thus, the organ weight differences observed were considered incidental and/or related to body weight changes and unrelated to administration of RTX.

Two unscheduled deaths occurred unrelated to test article administration, including a recovery study female at 2.5 µg RTX (Test Article 1) found dead on Day 2 and a recovery study female administered Control Article 2 euthanized on Day 13. The death of the animal administered Test Article 1 was attributed to aspiration-related foreign material/inflammation in the lung, whereas the death of the animal administered Control Article 2 could not be explained by gross or microscopic evaluation, and a relationship of the moribund condition to Control Article 2 could not be ruled out.

In conclusion, nerve block injection of RTX as a single dose to rats at doses of 0, 0.625, 2.5, or 10 µg resulted in no test article-related mortality, differences in organ weight, or gross observations. At >2.5 µg RTX there was a non-adverse microscopic change in the mammary gland (single cell necrosis), and at 10 µg RTX there was a microscopic change in the skeletal muscle (myofiber degeneration/necrosis), all of which fully recovered following a 14-day recovery period. A microscopic change related to Control Article 2 was noted in the administration site (mixed cell inflammation with or without myofiber degeneration/necrosis). All of these findings fully recovered following a 14-day recovery period.

What is claimed is:

1. A method of treating maladaptive pain, comprising peripherally perineurally administering resiniferatoxin (RTX) to a subject in need of treatment of maladaptive pain.

2. The method of claim 1, wherein the method comprises administering a dose of 0.1 μg to 100 μg of RTX, or a dose of RTX in the range of from 0.1-1 μg, 1-2 μg, 2-5 μg, 5-10 μg, 10-20 μg, 20-30 μg, 30-40 μg, 40-50 μg, 50-60 μg, 60-70 μg, 70-80 μg, 80-90 μg, or 90-100 μg.

3. The method of claim 1, wherein the RTX is administered perineurally to a single site, to a plurality of sites, to the sciatic nerve, to the saphenous nerve, to the femoral nerve, to the radial nerve, to the ulnar nerve, to the median nerve, to the musculocutaneous nerve, and/or to the palmar digital nerve; or wherein the RTX is administered perineurally to a plurality of sites that collectively correspond to sensory input from one or more digits, a foot or hand, a forelimb, a limb, and/or a joint.

4. The method of claim 1, wherein the subject is an amputee, or the subject suffers from phantom limb pain or stump pain; or wherein perineural administration targets one or more nerve fibers downstream of an amputation site.

5. The method of claim 1, wherein perineural administration targets at least two, three, four, or five nerve fibers downstream of an amputation site.

6. The method of claim 1, wherein the subject has abnormal nerve growth at nerve endings.

7. The method of claim 6, wherein perineural administration targets one or more nerve fibers downstream of a nerve with abnormal growth at its peripheral ending.

8. The method of claim 1, wherein perineural administration targets one or more nerve fibers downstream of a neuroma.

9. The method of claim 1, wherein the method comprises administering a pharmaceutical formulation comprising the RTX and a pharmaceutically acceptable carrier.

10. The method of claim 9, wherein the pharmaceutically acceptable carrier comprises
  a) water;
  b) polysorbate 80;
  c) polyethylene glycol;
  d) a sugar or sugar alcohol;
  e) mannitol;
  f) dextrose;
  g) a pharmaceutically acceptable salt; and/or
  h) a pharmaceutically acceptable buffer.

11. The method of claim 10, wherein the pharmaceutically acceptable carrier comprises a pharmaceutically acceptable buffer, and the pharmaceutically acceptable buffer is a phosphate buffer.

12. The method of claim 10, wherein the pharmaceutical formulation has a pH in the range of 6 to 7.6; or wherein the pharmaceutical formulation has a pH in the range of 6 to 6.4, 6.3 to 6.7, 6.4 to 6.8, 6.8 to 7.2, 7 to 7.4, or 7.2 to 7.6; or wherein the pharmaceutical formulation has a pH of 6.5 or 7.2.

13. The method of claim 10, wherein the concentration of RTX in the pharmaceutical formulation is in the range of 0.02-0.1 μg/ml or 0.1 to 300 μg/ml.

14. The method of claim 13, wherein the concentration of RTX in the pharmaceutical formulation is in the range of 0.02-0.1 μg/ml, 0.1-1 μg/ml, 1-5 μg/ml, 5-10 μg/ml, 10-20 μg/ml, 20-50 μg/ml, 50-100 μg/ml, 100-150 μg/ml, 150-200 μg/ml, 200-250 μg/ml, or 250-300 μg/ml.

15. The method of claim 10, wherein the concentration of RTX in the pharmaceutical formulation is in the range of 0.1-200 μg/ml, optionally wherein the concentration of RTX in the pharmaceutical formulation is in the range of 0.1-50 μg/ml.

16. The method of claim 1, wherein the RTX is administered in an injection volume of 0.05-10 ml, optionally wherein the injection volume is in the range of 0.05-0.2 ml, 0.2-0.5 ml, 0.5-1 ml, 1-2 ml, 2-5 ml, or 5-10 ml.

17. The method of claim 1, wherein the subject is a mammal; or wherein the subject is a cat, dog, horse, pig, ruminant, cow, sheep, goat, or domesticated mammal.

18. The method of claim 17, wherein the subject is a human.

19. The method of claim 1, wherein the treatment reduces local and central effects of the maladaptive pain.

20. The method of claim 1, wherein the subject had one or more behavioral symptoms of maladaptive pain prior to treatment and the treatment reduces or eliminates the one or more behavioral symptoms.

* * * * *